United States Patent [19]
Seed

[11] Patent Number: 6,133,025
[45] Date of Patent: Oct. 17, 2000

[54] COMPACT EPSTEIN-BARR VIRUS REPLICONS

[75] Inventor: Brian Seed, Boston, Mass.

[73] Assignee: The General Hospital Corporation, Boston, Mass.

[21] Appl. No.: 09/100,730

[22] Filed: Jun. 19, 1998

Related U.S. Application Data

[60] Provisional application No. 60/050,206, Jun. 19, 1997.
[51] Int. Cl.$^7$ .............................. C12N 15/00; C12N 7/00; C07H 21/04
[52] U.S. Cl. .................................. 435/320.1; 435/235.1; 435/325; 536/23.72
[58] Field of Search .............................. 435/320.1, 235.1, 435/325; 536/23.72; 424/199.1, 230.1

[56] References Cited

PUBLICATIONS

Belt et al., "Construction and properties of an Epstein–Barr–virus–derived cDNA expression vector for human cells," Gene 84:407–417, 1989.

Chittenden et al., "Functional limits of *ori*P, the Epstein–Barr virus plasmid origin of replication," Journal of Virology 63:3016–3025, 1989.

Inoue et al., "The domain of Epstein–Barr virus nuclear antigen 1 essential for binding to oriP region has a sequence fitted for the hypothetical basic–helix–loop–helix structure," Virology 182:84–93, 1991.

Jones et al., "Interaction of the lymphocyte–derived Epstein– Barr virus nuclear antigen EBNA–1 with its DNA–binding sites," Journal of Virology 63:101–110, 1989.

Kirchmaier and Sugden, "Dominant–negative inhibitors of EBNA–1 of Epstein–Barr virus," Journal of Virology 71:1766–1775, 1997.

Yates et al., "A cis–acting element from the Epstein–Barr viral genome that permits stable replication of recombinant plasmids in latently infected cells," Proc. Natl. Acad. Sci. USA 81:3806–3810, 1984.

Yates et al., "Stable replication of plasmids derived from Epstein–Barr virus in various mammalian cells," Nature 313:812–815, 1985.

Robert et al. J.of Virology, 1984, vol. 50, No. 3, pp. 822–831, Jun. 1984.

*Primary Examiner*—Ali Salimi
*Attorney, Agent, or Firm*—Karen L. Elbing; Clark & Elbing LLP

[57] ABSTRACT

Disclosed herein are nucleic acid sequences which support episomal replication in a mammalian cell. These nucleic acid sequences, which have a length of less than 3 kb, include (a) an OriP sequence and (b) an EBNA1 sequence operably linked to a promoter.

10 Claims, 3 Drawing Sheets

```
   1  AGATCTCCTT GGGAGGTGGC GGCATATGCA AAGGATAGCA CTCCCACTCT
  51  ACTACTGGGT ATCATATGCT GACTGTATAT GCATGAGGAT AGCATATGCT
 101  ACCCGGATAC AGATTAGGAT AGCATATACT ACCCAGATAT AGATTAGGAT
 151  AGCATATGCT ACCCAGATAT AGATTAGGAT AGCCTATGCT ACCCAGATAT
 201  AAATTAGGAT AGCATATACT ACCCAGATAT AGATTAGGAT AGCATATGCT
 251  ACCCAGATAT AGATTAGGAT AGCCTATGCT ACCCAGATAT AGATTAGGAT
 301  AGCATATGCT ACCCAGATAT AGATTAGGAT AGCATATGCT ATCCAGATCG
 351  CTGTTCCTTA GGACCCTTTT ACTAACCCTA ATTCGATAGC ATATGCTTCC
 401  CGTTGGGTAA CATATGCTAT TGAATTAGGG TTAGTCTGGA TAGTATATAC
 451  TACTACCCGG GAAGCATATG CTACCCGTTT AGGGTTAATA AGGGGATCT
 501  CCCCGCCCAG CGTCTTGTCA TTGGCGAACT CGAACACGCA GATGCAGTCG
 551  GGGCGGCGCG GTCCCAGGTC CACTTCGCAT ATTAAGGTGA CACGCGCGGC
 601  CTCGAACACA GCTGCAGGCC GCCATCATGG CACATGGACG AGGACGGGGA
 651  AGAGGACGAG GACGAGGAGG CGGAAGACCA GGAGCCCCGG GCGGCTCAGG
 701  ATCAGGGCCA AGACATAGAG ATGGTGTCCG GAGACCCCAA AAACGTCCAA
 751  GTTGCATTGG CTGCAAAGGG ACCCACGGTG AACAGGAGC AGGAGCAGGA
 801  GCGGGAGGGG CAGGAGCAGG AGGTGGAGGC CGGGGTCGAG GAGGCAGTGG
 851  AGGCCGGGGT CGAGGAGGTA GTGGAGGCCG GGTCGAGGA GGTAGTGGAG
 901  GCCGCCGGGG TAGAGGACGT GAAAGAGCCA GGGGGGGAAG TCGTGAAAGA
 951  GCCAGGGGGA GAGGTCGTGG ACGTGGAGAA AAGAGGCCCA GGAGTCCCAG
1001  TAGTCAGTCA TCATCATCCG GGTCTCCACC GCGCAGGCCC CCTCCAGGTA
```

FIGURE 1A

```
1051    GAAGGCCATT TTTCCACCCT GTAGGGAAG  CCGATTATTT TGAATACCAC

1101    CAAGAAGGCG GCCCAGATGG TGAGCCTGAC GTGCCCCCGC GCAGCGGGGG

1151    TCAGGGTGAT GGAGGCAGGC GCAAAAAAGG AGGGTGGTTT GGAAAGCATC

1201    GTGGTCAAGG AGGTTCCAAC CCGAAATTTG AGAACATTGC AGAAGGTTTA

1251    AGAGCTCTCC TGGCTAGGAG TCACGTAGAA AGGACTACCG ACGAAGGAAC

1301    TTGGGTCGCC GGTGTGTTCG TATATGGAGG TAGTAAGACC TCCCTTTACA

1351    ACCTAAGGCG AGGAACTGCC CTTGCTATTC CACAATGTCG TCTTACACCA

1401    TTGAGTCGTC TCCCCTTTGG AATGGCCCCT GGACCCGGCC CACAACCTGG

1451    CCCGCTAAGG GAGTCCATTG TCTGTTATTT CATGGTCTTT TTACAAACTC

1501    ATATATTTGC TGAGGTTTTG AAGGATGCGA TTAAGGACCT TGTTATGACA

1551    AAGCCCGCTC CTACCTGCAA TATCAGGGTG ACTGTGTGCA GCTTTGACGA

1601    TGGAGTAGAT TTGCCTCCCT GGTTTCCACC TATGGTGGAA GGGGCTGCCG

1651    CGGAGGGTGA TGACGGAGAT GACGGAGATG AAGGAGGTGA TGGAGATGAG

1701    GGTGAGGAAG GGCAGGAGTG ATGTAACTTG TTAGGAGACG ATGGATCC
```

FIGURE 1B
(SEQ ID NO: 1)

```
  1  GGATCCAAAA ATAAAATAAA ATAAAAATTA AAAAAAAAGT GTTGTGTCAC

51  ACAAAAAACC AACACACATT TTTTTTTGTT TTTATAAACC CTTTATTGTT

101  AAC
```

FIGURE 2
(SEQ ID NO: 2)

SEQUENCE LISTING

<160> NUMBER OF SEQ ID NOS: 2

<210> SEQ ID NO 1
<211> LENGTH: 1748
<212> TYPE: DNA
<213> ORGANISM: Epstein Barr Virus

<400> SEQUENCE: 1

```
agatctcctt gggaggtggc ggcatatgca aaggatagca ctcccactct actactgggt      60
atcatatgct gactgtatat gcatgaggat agcatatgct acccggatac agattaggat     120
agcatatact acccagatat agattaggat agcatatgct acccagatat agattaggat     180
```

-continued

```
agcctatgct acccagatat aaattaggat agcatatact acccagatat agattaggat      240
agcatatgct acccagatat agattaggat agcctatgct acccagatat agattaggat      300
agcatatgct acccagatat agattaggat agcatatgct atccagatcg ctgttccttg      360 ggacccttt actaaccca attcgatagc atatgcttcc cgttgggtaa catatgctat       420
tgaattaggg ttagtctgga tagtatatac tactacccgg gaagcatatg ctacccgttt      480
agggttaata aggggggtct ccccgcccag cgtcttgtca ttggcgaact cgaacacgca     540
gatgcagtcg gggcggcgcg gtcccaggtc cacttcgcat attaaggtga cacgcgcggc     600
ctcgaacaca gctgcaggcc gccatcatgg cacatggacg aggacgggga agaggacgag     660
gacgaggagg cggaagacca ggagcccggg gcggctcagg atcagggcca agacatagag     720
atggtgtccg gagaccccaa aaacgtccaa gttgcattgg ctgcaaaggg acccacggtg     780
gaacaggagc aggagcagga gcgggagggg caggagcagg aggtggaggc cggggtcgag     840
gaggcagtgg aggccgggt cgaggaggta gtggaggccg gggtcgagga ggtagtggag      900
gccgccgggg tagaggacgt gaaagagcca gggggggaag tcgtgaaaga gccaggggga    960
gaggtcgtgg acgtggagaa aagaggccca ggagtcccag tagtcagtca tcatcatccg    1020
ggtctccacc gcgcaggccc cctccaggta gaaggccatt tttccaccct gtaggggaag    1080
ccgattattt tgaataccac caagaaggcg gcccagatgt tgagcctgac gtgccccgc     1140 gcagcggggg tcagggtgat ggaggcaggc gcaaaaaagg agggtggttt ggaaagcatc    1200
gtggtcaagg aggtccaac ccgaaatttg agaacattgc agaaggttta agagctctcc    1260
tggctaggag tcacgtagaa aggactaccg acgaaggaac ttgggtcgcc ggtgtgttcg    1320
tatatggagg tagtaagacc tccctttaca acctaaggcg aggaactgcc cttgctattc    1380
cacaatgtcg tcttacacca ttgagtcgtc tccctttgg aatggcccct ggacccggcc    1440
cacaacctgg cccgctaagg gagtccattg tctgttatt catggtctt ttacaaactc     1500 atatatttgc tgaggttttg aaggatgcga ttaaggacct tgttatgaca agcccgctc    1560 ctacctgcaa tatcaggtg actgtgtgca gctttgacga tggagtagat ttgcctcct    1620 ggtttccacc tatggtggaa gggctgccg cggagggtga tgacggagat gacggagatg    1680
aaggaggtga tggagatgag ggtgaggaag ggcaggagtg atgtaacttg ttaggagacg    1740
atggatcc                                                             1748
```

<210> SEQ ID NO 2
<211> LENGTH: 103
<212> TYPE: DNA
<213> ORGANISM: Artificial Sequence
<220> FEATURE:
<223> OTHER INFORMATION: Bidirectional polyadenylation sequence

<400> SEQUENCE: 2

```
ggatccaaaa ataaaataaa ataaaaatta aaaaaaaagt gttgtgtcac acaaaaaacc      60
aacacacatt ttttttttgtt tttataaacc ctttattgtt aac                     103
```

COMPACT EPSTEIN-BARR VIRUS REPLICONS

CROSS REFERENCE TO RELATED APPLICATIONS

The present application claims benefit of the filing date of U.S. Provisional Application No. 60/050,206, filed Jun. 19, 1997, the entire contents of which are incorporated herein by reference.

BACKGROUND OF THE INVENTION

Epstein-Barr virus (EBV) is a human herpes virus with a latent phase characterized by stable episomal propagation of a circular form of the viral DNA. Two discontinuous DNA elements are required for latent phase replication, the cis-acting origin of replication, OriP, and the Epstein-Barr Nuclear Antigen 1 (EBNA1), the sole virally encoded protein necessary for replication (Yates et al., Proc. Natl. Acad. Sci. USA 81:3806–10, 1984; Yates et al., Nature 313:812–5, 1985). Most EBV vectors are very large, on the order of 10 kb or more (without insert), because of the large size of the EBNA1 and OriP segments. The size of most existing EBV EBNA1 and OriP segments has interfered with the development of improved expression vectors and the creation of compact gene expression and persistence cassettes which can be embedded in other gene delivery vehicles, such as retroviruses or adenoviruses.

SUMMARY OF THE INVENTION

In general, the invention features a nucleic acid sequence which supports episomal replication in a mammalian cell. This nucleic acid sequence includes (a) an OriP sequence (for example, an OriP fragment) and (b) an EBNA1 sequence (for example, an EBNA fragment) operably linked to a promoter, and the nucleic acid sequence has a length of less than 3 kb, preferably less than 2 kb, and, most preferably, less than 1.8 kb.

In preferred embodiments, the OriP sequence includes approximately residues 1–495 of SEQ ID NO: 1; the EBNA1 sequence includes approximately residues 627–1718 of SEQ ID NO: 1; the nucleic acid sequence further includes a polyadenylation consensus sequence (for example, approximately the sequence of SEQ ID NO: 2); and the promoter is a viral promoter.

In related aspects, the invention also features vectors and cells (for example, mammalian cells, and preferably human cells) that include such nucleic acid sequences.

By "an OriP fragment" is meant a nucleic acid sequence which provides for OriP-mediated episomal replication but which is deleted for at least a portion of the nucleic acid sequence associated with the full-length origin.

By "an EBNA fragment" is meant a nucleic acid sequence which encodes an EBNA protein which provides for episomal replication but which is deleted for at least a portion of the nucleic acid sequence associated with the full-length viral gene.

DESCRIPTION OF THE DRAWINGS

FIGS. 1A and 1B is the sequence of a shortened EBV OriP and EBNA-1 cassette.

FIG. 2 is the sequence of a compact synthetic bidirectional polyadenylation sequence which may be used in conjunction with a compact EBV replicon.

DETAILED DESCRIPTION

After extensive deletion and mutagenesis, it has been found possible to embed the cis- and trans-acting functions necessary for EBV episomal replication into a fragment of less than 2 kb. In particular, an exemplary fragment of 1748 base pairs which acts as a compact EBV replicon is shown in FIG. 1 (SEQ ID NO: 1). This fragment contains all sequences needed for efficient expression of the EBNA-1 protein, with the exception of a polyadenylation consensus sequence. The fragment is a Bgl2 to BamH1 segment which contains the OriP element between residues 1 and 495, a modified promoter from the Herpes simplex virus 1 thymidine kinase gene between residues 496 to 616, and the coding sequence for a deleted and modified EBNA1 gene between residues 627 and 1718. Plasmid vectors based on this sequence replicate as episomes in the nucleus of transfected cells of nonrodent origin (Yates et al., Nature 313:812–5, 1985).

To minimize overall sequence length, the above fragment was designed to be inserted upstream from a bidirectional polyadenylation sequence in an appropriate vector. An example of a compact synthetic bidirectional polyadenylation sequence is provided in FIG. 2 (SEQ ID NO: 2).

Compact EBV replicons find use in gene therapy vectors, for example, in gene delivery vehicles such as expression vectors.

Other embodiments are within the claims.

---

What is claimed is:

1. A nucleic acid sequence which supports episomal replication in a mammalian cell, said nucleic acid sequence comprising (a) a cis-acting Epstein-Barr virus origin of replication sequence (OriP) and (b) an Epstein-Barr Nuclear Antigen 1 (EBNA1) sequence operably linked to a promoter, said nucleic acid sequence having a length of less than 3 kb.

2. The nucleic acid sequence of claim 1, said nucleic acid having a length of less than 2 kb.

3. The nucleic acid sequence of claim 1, said nucleic acid having a length of less than 1.8 kb.

4. The nucleic acid sequence of claim 1, wherein said OriP sequence comprises residues 1–495 of SEQ ID NO: 1.

5. The nucleic acid sequence of claim 1, wherein said EBNA1 sequence comprises residues 627–1718 of SEQ ID NO: 1.

6. The nucleic acid sequence of claim 1, said nucleic acid sequence further comprising a polyadenylation consensus sequence.

7. The nucleic acid sequence of claim 6, wherein said polyadenylation consensus sequence comprises SEQ ID NO: 2.

8. The nucleic acid sequence of claim 1, wherein said promoter is a viral promoter.

9. A vector comprising the nucleic acid sequence of claim 1, said vector being capable of replicating as an episome in the nucleus of a transfected cell.

10. A cell comprising the nucleic acid sequence of claim 1.

* * * * *